United States Patent [19]

Ries

[11] Patent Number: 4,574,061
[45] Date of Patent: Mar. 4, 1986

[54] ALKOXY ARYL SULFONATE SURFACTANTS

[75] Inventor: Donald G. Ries, Richmond, Tex.

[73] Assignee: Nalco Chemical Company, Oak Brook, Ill.

[21] Appl. No.: 729,775

[22] Filed: May 2, 1985

[51] Int. Cl.$^4$ ............................................. C07C 143/42
[52] U.S. Cl. .............................. 260/512 C; 260/512 R; 252/8.55 D; 252/553
[58] Field of Search ......................... 260/512 R, 512 C

[56] References Cited

U.S. PATENT DOCUMENTS

| | | | |
|---|---|---|---|
| 3,812,178 | 5/1974 | Weedon | 260/512 R |
| 4,042,618 | 8/1977 | Davis | 260/512 R |
| 4,073,802 | 2/1978 | Hartmann | 260/512 R |
| 4,358,368 | 11/1982 | Hellston | 260/501.11 |
| 4,436,672 | 3/1984 | Naylor | 260/512 R |

OTHER PUBLICATIONS

CA, 48, 1711i, (1954).
CA, 55, 21628a, (1960).
CA, 69, 78644, (1968).
Tenside 5, 193, (1968).
CA, 74, 99561, (1971).
Tenside 7, 249, (1970).
CA, 78, 147565, (1973).
CA, 81, 136733, (1974).
CA, 81, 92192, (1974).
CA, 84, 76121, (1976).
CA, 85, 77887, (1976).
CA, 88, 24194, (1978).
CA, 88, 169776, (1978).
CA, 49, 9298g, (1955).
CA, 55, 24680h, (1961).
CA, 78, 84025h, (1973).
CA, 86, 17695, (1977).
CA, 98, 76061, (1983).

Primary Examiner—Nicky Chan
Attorney, Agent, or Firm—John G. Premo; Donald G. Epple

[57] ABSTRACT

The invention is directed to novel sulfonates having the following structural formula:

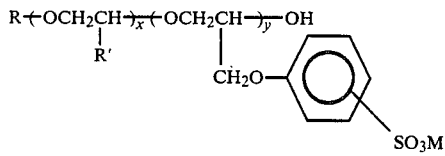

where in the above formula, R is a $C_6$–$C_{20}$ hydrocarbon or substituted hydrocarbon group, R' is from the group consisting of hydrogen or lower alkyl radicals of from 1–4 carbon atoms, x is an integer having the value between 0–50, y is an integer within the range of 1–5, and M is a metal cation.

3 Claims, No Drawings

ALKOXY ARYL SULFONATE SURFACTANTS

INTRODUCTION

Anionic surfactants are useful in a variety of application areas. These surfactants are generally of two types: sulfates of alcohols or of ethoxylated alcohols and alkyl or alkylaromatic sulfonates. The sulfonates are preferred for some applications, especially those involving low pH and/or high temperature, since sulfates suffer from an inherent lack of thermal and hydrolytic stability which severly limits their usefulness in these areas.

Sulfonates are generally prepared by adding $SO_3$ to a hydrocarbon acceptor.

It is known that alkoxybenzene-sulfonic acid salts could be prepared from alkylhalides and phenolsulfonic acid salts. However, surfactant range alkylhalides are generally too expensive for practical use.

THE INVENTION

It has been found that novel sulfonates can be produced by reacting alcohols or alkoxylated alcohols with either epichlorohydrin or its equivalent, epibromohydrin, to produce an ether alkyl halide which is then reacted with phenol sulfonic acid.

This reaction mechanism is best illustrated by the following reactions. Formula 1, which is the starting alkyl ether halide, is reacted with phenol sulfonic acid to produce the novel sulfonates of the invention, Formula 2.

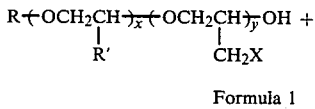

Formula 1

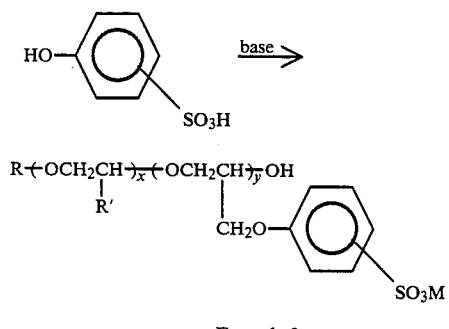

Formula 2

In Formulas 1 and 2 above, R is a $C_6$–$C_{20}$ hydrocarbon or substituted hydrocarbon group. It may be an alkyl, substituted alkyl, aromatic alkaryl, or alkylaromatic group. Preferably it is a $C_6$–$C_{20}$ aliphatic straight or branched chain hydrocarbon group.

R' is from the group consisting of hydrogen or lower alkyl radicals of from 1–4 carbon atoms.

x is an integer between 0–50, preferably 0–20, and most preferably 0–20.

y is an integer, preferably having a value of 1, but it may have a value within the range of 1–5.

M is a cation and is preferably sodium or potassium. It may be another metal.

THE STARTING ALCOHOLS

The starting alcohols that are used to react with the epichloro or epibromohydrin may be selected from a large group of alcohols. The alcohols most preferably are $C_6$–$C_{20}$ straight or branched chain hydrocarbon alcohols of the types produced by the well known oxo reaction. These alcohols may be used as such or subjected to reaction with simple epoxides such as ethylene or propylene oxide to produce an ether alcohol. Either the simple alcohol or the epoxide reacted alcohol is then further reacted with epichlorohydrin to produce the alkyl ether halides of the type shown in Formula 1.

A typical preparative scheme used to produce the starting alcohols of the type shown in Formula 1 is best illustrated by the following example:

EXAMPLE 1

These intermediates are prepared from alcohols or alkoxylated alcohols and epichlorohydrin or epibromohydrin using standard procedures well documented in the literature. In the laboratory, a $BF_3$-etherate as catalyst was used. Others could also be used. A typical laboratory procedure is given for preparation of a $C_{12}$alcohol-epi adduct:

To a 500 ml flask equipped with stirrer, condenser, $N_2$ inlet, thermometer and addition funnel, is added 100 g (0.538 equivalents) of the $C_{12}$ alcohol. The alcohol is heated to 100°–110° while stirring and purging with $N_2$. Purging is continued for 1 hr. After cooling to 80° while maintaining a $N_2$ atmosphere, 0.75 ml of boron trifluoride etherate is added. This is followed by 74.6 g (0.807 eq) epichlorohydrin added over 1 hour at 80°–100°. The reaction mixture is stirred for an additional 3 hours at 100°–110° to give the adduct.

Products of the type formed by the reaction scheme illustrated in Example 1 would then be reacted with phenol sulfonate in accordance with the general reaction schemes which are described below as Example 2.

EXAMPLE 2

The reaction is run in the presence of 2 equivalents of a base such as NaOH, KOH, $Na_2CO_3$, $K_2CO_3$. One equivalent is used to salt the sulfonic acid; the other enters into the reaction to form the ether. In addition, a small amount of an iodide salt such as NaI or KI is added to aid or promote the reaction.

The solvent system is generally an alcohol/water mix such as isopropanol/water, although water can be used alone. Other aprotic polar solvents could also be used, e.g. DMSO, DMF.

In the laboratory the reaction was generally run by mixing the components in a mini-Parr autoclave, heating to 130° C. and stirring at that temperature for 6–7 hours. At the end of the run the product was diluted to 10 to 20% active with water or water/isopropanol solvent.

To illustrate, many useful surfactants may be produced in accordance with the invention using the preparative techniques of Examples 1 and 2. The following are given by way of additional Examples.

GLOSSARY

Comp. 1: $C_{12}$–$C_{14}$ linear chain alcohol reacted with 10 moles ethylene oxide.

Comp. 2: $C_{12}$ linear chain alcohol reacted with 3 moles ethylene oxide.

Comp. 3: $C_{12}$–$C_{15}$ mixed alkyl alcohol.

Comp. 4: $C_{12}$ alcohol.

Comp. 5: $C_{10}$ alcohol.

Comp. 6: $C_8$ alcohol.

Comp. 7: C6–C10 alcohol.
Comp. 8: Nonyl phenol.

TABLE I

Surface Tension of Phenolsulfonic Acid Derived Surfactants

| Example No. | EPI Adduct | Cation | Diluent | δ, Dynes/cm, At Wt. % Active | |
|---|---|---|---|---|---|
| | | | | 0.10 | 0.01 |
| 3. | Comp. 1 | K | DI H2O | 32.8 | 34.4 |
| | " | " | 2% KCl | 31.9 | 33.0 |
| 4. | Comp. 2 | " | DI H2O | 31.1 | 32.6 |
| | " | " | 2% KCl | | |
| | " | Na | DI H2O | 33.3 | 36.0 |
| | " | " | 2% KCl | 29.6 | 30.6 |
| 5. | Comp. 3 | K | DI H2O | | |
| | " | " | 2% KCl | | |
| | " | Na | DI H2O | 28.6 | 29.5 |
| | " | " | 2% KCl | 28.4 | 28.4 |
| 6. | Comp. 4 | K | DI H2O | 27.7 | 28.7 |
| | " | " | 2% KCl | | |
| | " | Na | DI H2O | 29.0 | 29.2 |
| | " | " | 2% KCl | 27.3 | 28.0 |
| 7. | Comp. 5 | K | DI H2O | 28.3 | 33.2 |
| | " | " | 2% KCl | | |
| | " | Na | DI H2O | 28.7 | 33.9 |
| | " | " | 2% KCl | 27.5 | 28.9 |
| 8. | Comp. 6 | K | DI H2O | 32.8, 31.4 | 45.1 |
| | " | " | 2% KCl | 29.5 | 40.9 |
| 9. | Comp. 7 | " | DI H2O | 31.6, 30.2 | 39.7 |
| | " | " | 2% KCl | 28.9 | 31.3 |
| 10. | Comp. 8 | " | DI H2O | | |
| | " | " | 2% KCl | | |

TABLE II

Surface Tension vs. Concentration of Some Phenolsulfonic Acid Derived Surfactants

| Example No. | EPI Adduct | Cation | Diluent | Surface Tension, Dynes/cm, At Wt. % Active | | | | | | | | | |
|---|---|---|---|---|---|---|---|---|---|---|---|---|---|
| | | | | 1.00 | 0.50 | 0.25 | 0.10 | 0.05 | 0.025 | 0.01 | 0.005 | 0.0025 | 0.001 |
| 11. | Comp. 2 | K | DI H2O | 30.3 | 30.6 | 30.7 | 31.1 | 31.4 | 32.1 | 32.6 | 33.3 | 36.3 | 46.0 |
| 12. | Comp. 4 | K | DI H2O | — | 27.7 | 27.4 | 27.7 | 28.5 | 28.3 | 28.7 | 29.5 | 34.6 | — |
| 13. | Comp. 5 | K | DI H2O | 28.4 | 28.7 | 28.5 | 28.3 | 29.0 | 30.3 | 33.2 | 37.9 | 46.6 | — |
| 14 | Comp. 6 | K | DI H2O | 29.4 | 29.1 | 29.2 | 32.8 | 36.6 | 41.6 | — | — | — | — |
| | | | 2% KCl | 28.7 | 28.8 | 28.8 | 29.5 | 30.5 | 34.4 | 40.9 | — | — | — |
| 15. | Comp. 7 | K | DI H2O | 30.9 | 30.8 | 30.7 | 31.6 | 33.3 | 35.5 | — | — | — | — |
| | | | 2% KCl | 29.8 | 29.8 | 29.8 | 28.9 | 29.5 | 30.0 | 31.3 | 38.2 | 45.9 | — |

It should be noted from Tables I and II that the compositions of the invention are effective in reducing the surface tension of water.

These surfactants have many uses in, such as for instance, stimulating oil wells, production of detergents for industrial and home use, emulsion breakers, and many others.

Having thus described my invention, I claim:

1. A sulfonate having the structural formula:

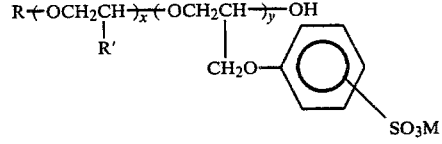

where in the above formula, R is a C6–C20 alkyl or alkaryl group, R' is from the group consisting of hydrogen or lower alkyl radicals of from 1–4 carbon atoms, x is an integer having the value between 0–50, y is an integer within the range of 1–5, and M is from the group consisting of sodium and potassium.

2. The sulfonate of claim 1 where R is a C6–C20 alkyl group, R' is either hydrogen or methyl, x is within the range of 0–20, y is 1.

3. The sulphonate of claim 1 where R is a C6–C20 alkaryl group.

* * * * *